United States Patent [19]
Pautard-Cooper et al.

[11] Patent Number: 5,936,090
[45] Date of Patent: *Aug. 10, 1999

[54] PROCESSES FOR THE REDUCTION OF IMIDE ESTER FUNCTIONALITY

[75] Inventors: Anne Pautard-Cooper, Tarpon Springs, Fla.; Philip Franklin Sims, Cherryville; James Anthony Schwindeman, Lincolnton, both of N.C.

[73] Assignee: FMC Corporation, Philadelphia, Pa.

[*] Notice: This patent is subject to a terminal disclaimer.

[21] Appl. No.: 08/861,641

[22] Filed: May 22, 1997

Related U.S. Application Data

[60] Provisional application No. 60/018,298, May 24, 1996.

[51] Int. Cl.⁶ .................. C07D 211/22; C07D 211/32
[52] U.S. Cl. ........................... 546/220; 546/240
[58] Field of Search ...................... 546/220, 240

[56] References Cited

U.S. PATENT DOCUMENTS 4,902,801  2/1990  Faruk et al. .................. 546/220

FOREIGN PATENT DOCUMENTS

| | | |
|---|---|---|
| 0 223 334 | 5/1987 | European Pat. Off. . |
| 0 374 675 | 6/1990 | European Pat. Off. . |
| H3-200762 | 9/1991 | Japan . |
| WO 94/21609 | 9/1994 | WIPO . |

OTHER PUBLICATIONS

Greenwood, N.N. et al, Chemistry of the Elements, 1984, Pergamon Press, pp. 256–261.

L. Weber, "Functionalization of Living Polymers—Results and Problems," Makromol. Chem., Macromol. Symp. 3, 317–329 (1986).

Primary Examiner—Ba K. Trinh
Attorney, Agent, or Firm—Alston & Bird LLP

[57] ABSTRACT

The present invention provides improved processes for the chemical reduction of imide esters to the corresponding amino alcohols with yields greater than 76%. A specific range of ethereal to hydrocarbon solvent ratio is used. The improved yield can be achieved using as a reducing agent lithium aluminum hydride or the less costly sodium aluminum hydride in combination with an additive such as lithium chloride.

16 Claims, No Drawings

PROCESSES FOR THE REDUCTION OF IMIDE ESTER FUNCTIONALITY

CROSS-REFERENCE TO RELATED APPLICATIONS

This application is related to commonly owned Provisional Application Ser. No. 60/018,298, filed May 24, 1996, and claims the benefit of its earlier filing date under 35 U.S.C. 119(e).

FIELD OF THE INVENTION

The present invention relates to processes for reducing imide esters to corresponding amino alcohols.

BACKGROUND OF THE INVENTION

The reduction of the imide ester (+/−) trans-3-ethoxy-carbonyl-4-(4'-fluorophenyl)-N-methylpiperidine-2,6-dione (I) to the corresponding amino alcohol (+/−) trans-4-(4'-fluorophenyl)-3-hydroxymethyl-N-methylpiperidine (II) is known. The chemical reduction of substrate I involves the conversion of the imide functionality into an amine and that of the ester group into an alcohol, resulting in amino alcohol II. This amino alcohol is a useful chemical intermediate in the synthesis of more complex organic compounds of medicinal value.

U.S. Pat. No. 4,902,801 describes the reduction of substrate I with lithium aluminum hydride (LAH) in a reaction concentration of approximately 0.33 Molar, with the solvent composition as 14% tetrahydrofuran and 86% toluene by volume. Yields reported for these specific conditions range from 65% to 75% isolated. In a similar example an increase in the percent tetrahydrofuran to 100%, that is, with no toluene present, still resulted in only a 65% isolated yield. Lithium aluminum hydride is a powerful but expensive reducing agent, making higher reaction yields and lower reagent cost critical for economic feasibility and wider industrial use.

Japanese Unexamined Patent H3-200762 to Maemoto et al. describes the reduction of the imide N-benzylmalic acid imide using sodium aluminum hydride with yields ranging from 52% to 63%. Reduction of imide (I) with sodium aluminum hydride alone gives similar yields of 50% or less.

SUMMARY OF THE INVENTION

The present invention provides an improved process for the chemical reduction of imide esters to the corresponding amino alcohols. The processes of the invention can provide increased yields of the desired amino alcohol (with yields greater than 76%) and lower reagent costs. In the process of the invention, a specific range of ethereal to hydrocarbon solvent ratio is used to achieve this yield increase. Higher reaction concentrations can also be employed successfully. Various reducing agents can be used, such as lithium aluminum hydride, the less costly sodium aluminum hydride in combination with an additive, for example, lithium chloride, and the like.

DETAILED DESCRIPTION OF THE INVENTION

The present invention provides an improved process for the chemical reduction of imide esters, singly or mixtures thereof, of the general formula

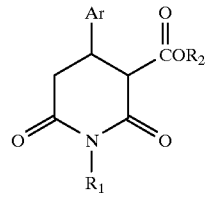

wherein:
Ar represents an aryl or substituted aryl group

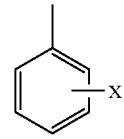

in which X can be hydrogen, C1–C4 alkyl, C1–C4 alkoxy, trifluoroalkyl, hydroxy, halogen, preferably fluorine, methylthio or arylalkyloxy;
$R^1$ is hydrogen, C1–C4 alkyl, or arylalkyl; and
$R^2$ is C1–C4 alkyl,
to the corresponding amino alcohols, singly or mixtures thereof, of the general formula

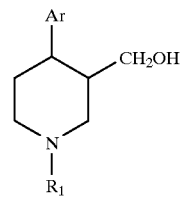

in which $R^1$ and Ar are the same as defined above. Preferably, X is hydrogen or fluorine, $R^1$ is hydrogen or methyl, and $R^2$ is methyl or ethyl.

For example, unexpectedly, it was discovered that the reduction of the imide ester (+/−) trans 3-ethoxy or 3-methoxy carbonyl-4-(4'-fluorophenyl)-N-methyl-piperidine-2,6-dione (I) resulted in the production of the amino alcohol (+/−) trans-4-(4'-fluorophenyl)-3-hydroxymethyl-N-methylpiperidine (II) with isolated yields greater than 76%. The higher yields obtained by this process result in lower raw material costs and minimization of unwanted by-products. In addition, it was discovered that the reduction could be performed at higher concentrations than described in the prior art, with no deleterious effect on the yield or quality of product. Higher throughput on an industrial scale and minimization of cycle time result from the use of higher concentrations.

The yields were obtained under certain specific reaction conditions. The substrate (I) was reduced with a suitable reducing agent, such as but not limited to lithium aluminum hydride, the reducing agent mixture of sodium aluminum hydride and an additive, such as lithium chloride, and the like. The reaction concentration ranged from approximately 7 to 10 ml of solvent per gram of substrate. The proportion of ethereal to hydrocarbon solvent ranged from 40% to 70% ethereal solvent in hydrocarbon solvent by volume. The reduction can be performed from room temperature to solvent reflux temperatures.

The amino alcohols can be obtained as a mixture of enantiomers. The compounds can be resolved into their enantiomeric forms by conventional methods, such as by use of an optically active acid, such as (+)-2'-nitrotartranilic acid, (−)-di-p-toluoyltartaric acid, and the like. Alternatively, the optically active form of the compound can be produced without requiring subsequent resolution.

These results for the reduction of (+/−) trans 3-ethoxy carbonyl-4-(4'-fluorophenyl)-N-methylpiperidine-2,6-dione (I) are summarized in the table below:

| Reference | Reducing Agent | % Ethereal Solvent | % Hydrocarbon Solvent | % Yield of II |
|---|---|---|---|---|
| 4,902,801 (Example 5) | $LiAlH_4$ | 100 | 0 | 65 |
| 4,902,801 (Example 7) | $LiAlH_4$ | 14 | 86 | 65–75 |
| Example 1 (Invention) | $LiAlH_4$ | 42 | 58 | 89.0 |
| Example 2 (Invention) | $NaAlH_4$/LiCl | 44 | 56 | 82.7 |
| Example 3 (Invention) | $NaAlH_4$/LiCl | 55 | 45 | 85.5 |
| Example 4 (Invention) | $NaAlH_4$/LiCl | 45 | 55 | 85.4 |
| Example 5 (Invention) | $NaAlH_4$/LiCl | 56 | 44 | 83.1 |
| Comparative Example | $NaAlH_4$/LiCl | 38 | 62 | 72.0 |

Examples of ethereal solvents include, but are not limited to, tetrahydrofuran, 2-methyltetrahydrofuran, diethyl ether, dibutyl ether, methyl t-butyl ether, diethoxymethane, dimethoxyethane and other glyme solvents, and mixtures thereof. Examples of hydrocarbon solvents include, but are not limited to, toluene, benzene, hexanes, heptane, xylene, ethyl benzene, and the like, and mixtures thereof. Optionally, additives other than lithium chloride can be used, such as, but not limited to, LiBr, $AlCl_3$, HCl, $TiCl_4$, $AlBr_3$, $TiBr_4$, $LiAlH_4$, $NaBH_4$, $AlH_3$, $THF-BH_3$, alcohols such as methanol, ethanol, isopropanol, t-butanol, ethereal alcohols and/or their corresponding metal alkoxides, and mixtures thereof. The additives can be employed in 0.01 equivalents up to and including 5.0 equivalents.

The following examples further illustrate the invention.

EXAMPLE 1

Reduction with Lithium Aluminum Hydride 0.47 Molar

A 500 ml, three-necked, jacketed flask was equipped with a mechanical stirrer, a 125 ml pressure-equalizing addition funnel, and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. The flask was charged with tetrahydrofuran, 70 ml. This solution was stirred at 350 RPMs and cooled to 0° C. with a circulating chiller. Lithium aluminum hydride, 8.51 grams of 95% assay (2.70 equivalents, 213 mmole) was added to the reactor. An immediate exotherm of 45° C. was noted, which quickly subsided. Toluene, 24 ml, was then added. This suspension was stirred at 0° C. for an additional 10 minutes. A dry, 250 ml, single-necked flask was fitted with a large, egg-shaped magnetic stir bar, and an argon inlet. This flask was purged with argon, then charged with 23.3 grams of (+/−) trans 3-ethoxy carbonyl-4-(4'-fluorophenyl)-N-methyl-piperidine-2,6-dione (I) (1.00 equivalent, 79 mmole) and 65 ml of toluene. This suspension was stirred at room temperature. This solution was transferred to the addition funnel. The 250 ml flask was rinsed with additional toluene, 8 ml, and this was added to the additional funnel. The imide-ester solution was added dropwise. This resulted in a very exothermic reaction. The feed rate was adjusted to maintain the reaction temperature at below 20° C. Total imide-ester feed time was 54 minutes. After the end of the feed, the reaction mixture was heated to 65° C. for two hours, then recooled to 0° C. The speed of the agitator was increased to 500 RPMs. Additional toluene, 85 ml, was added. This was followed by slow addition of 9 ml of water. The reaction mixture got very thick at the end of this addition. Aqueous sodium hydroxide, 15%, 9 ml, was then added dropwise. The solid started to break up at the end of this addition. Water, 18 ml, was then added dropwise. At the end of this feed, the reaction mixture was warmed to 27° C., and the stirrer was slowed to 350 RPMs. The reaction mixture was stirred at 27° C. for one hour, then the byproduct solids were collected on a Büchner funnel. The solids were reslurried with toluene (2×30 ml). The desired product (II) was isolated from the combined filtrates, washed, air dried, then dried in a vacuum desiccator overnight.

This afforded a white solid, yield=15.71 grams, 89.0%.

EXAMPLE 2

Reduction with Sodium Aluminum Hydride/ Lithium Chloride 0.44 Molar

A 500 ml, four-necked, round bottom flask was equipped with a mechanical stirrer, a 125 ml pressure-equalizing addition funnel, a Teflon® stopper and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. Lithium chloride, 10.00 grams (3.00 equivalents, 236.8 mmole) was added. The flask was then charged with tetrahydrofuran, 70 ml. This solution was stirred at 350 RPMs for thirty minutes. Sodium aluminum hydride, 12.80 grams of 90% assay (2.70 equivalents, 213.3 mmole) slurried in toluene, 24 ml, was added, and this suspension was stirred at room temperature for one hour then cooled to 10° C. A dry, 250 ml, single-necked flask was fitted with a large, egg-shaped magnetic stir bar, and an argon inlet. This flask was purged with argon, then charged with 23.3 grams of (+/−) trans 3-ethoxy carbonyl-4-(4'-fluorophenyl)-N-methyl-piperidine-2,6-dione (I) (1.00 equivalent, 79 mmole) and 65 ml of toluene. This suspension was stirred at room temperature. The solution was transferred to the addition funnel. The imide-ester solution was added dropwise. This resulted in a very exothermic reaction. The feed rate was adjusted to maintain the reaction temperature at below 20° C. The reaction mixture was heated to 75° C. for two hours, then recooled to 10° C. Additional toluene, 75 ml, was added. This was followed by slow addition of 9 ml of water. The reaction mixture got very thick at the end of this addition. Aqueous sodium hydroxide, 15%, 9 ml, was then added dropwise. This solid started to break up at the end of this addition. Water, 18 ml, was then added dropwise. At the end of this feed, the reaction mixture was warmed to 65° C. for thirty minutes and then the reaction mixture was then cooled to room temperature, then the byproduct solids were collected on a Büchner funnel. The solids were reslurried with toluene (2×30 ml). The desired product (II) was isolated from the combined filtrates, washed, air dried, then dried in a vacuum desiccator overnight.

This afforded a white solid, yield=14.59 grams, 82.7%.

EXAMPLE 3

Reduction with Sodium Aluminum Hydride/ Lithium Chloride 0.38 Molar

A 500 ml, four-necked, round bottom flask was equipped with a mechanical stirrer, a 125 ml pressure-equalizing addition funnel, a Teflon® stopper and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. Lithium chloride, 9.83 grams (2.64 equivalents, 231.90 mmole) was added. The flask was then charged with tetrahydrofuran, 67 ml. This solution was stirred at 350 RPMs. Sodium aluminum hydride, 11.98 grams of 95% assay (2.40 equivalents, 210.82 mmole) slurried in toluene, 21 ml, was added to the reactor. Additional tetrahydrofuran, 61 ml, was added and this suspension was stirred at room temperature for ninety minutes. Toluene, 6 ml, was then added. This suspension was cooled to 10° C. and stirred for an additional thirty minutes. A dry, 250 ml., single-necked flask was fitted with a large, egg-shaped magnetic stir bar, and an argon inlet. The flask was purged with argon, then charged with 25.9 grams of (+/−) trans 3-ethoxy carbonyl-4-(4'-fluorophenyl)-N-methyl-piperidine-2,6-dione (I) (1.00 equivalent, 88 mmole) and 69 ml of toluene. This suspension was stirred at room temperature. This solution was transferred to the addition funnel. The imide-ester solution was added dropwise. This resulted in a very exothermic reaction. The feed rate was adjusted to maintain the reaction temperature at below 20° C. After the end of the feed, the 250 ml flask was rinsed with additional toluene, 7 ml, and this was added to the addition funnel. The reaction mixture was heated to 75° C. for three hours, then recooled to 10° C. Additional toluene, 50 ml, was added. The speed of the agitator was increased to 500 RPMs. This was followed by slow addition of 9 ml of water. The reaction mixture got very thick at the end of this addition. Aqueous sodium hydroxide, 15%, 9 ml, was then added dropwise. The solid started to break up at the end of this addition. Water, 18 ml, was then added dropwise. At the end of this feed, the reaction mixture was warmed to 60° C. for twenty minutes and the stirrer was slowed to 350 RPMs. The reaction mixture was then cooled to 40° C., then the byproduct solids were collected on a Büchner funnel. The solids were reslurried with reslurried with toluene (2×31 ml). The desired product (II) was isolated from the combined filtrates, washed, air dried, then dried in a vacuum desiccator overnight.

This afforded a white solid, yield=16.80 grams, 85.5%.

EXAMPLE 4

Reduction with Sodium Aluminum Hydride/ Lithium Chloride 0.38 Molar

A 500 ml, four-necked, round bottom flask was equipped with a mechanical stirrer, a 125 ml pressure-equalizing addition funnel, a Teflon® stopper and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. Lithium chloride, 9.85 grams (2.64 equivalents, 232.36 mmole) was added. The flask was then charged with tetrahydrofuran, 67 ml. This solution was stirred at 350 RPMs. Sodium aluminum hydride, 12.01 grams of 95% assay (2.40 equivalents, 211.24 mmole) slurried in toluene, 21 ml, was added to the reactor. Additional tetrahydrofuran, 39 ml, was added and this suspension was stirred at room temperature for fifty minutes. Toluene, 31 ml, was then added. This suspension was cooled to 10° C. and stirred for an additional five minutes. A dry, 250 ml., single-necked flask was fitted with a large, egg-shaped magnetic stir bar, and an argon inlet. This flask was purged with argon, then charged with 25.9 grams of (+/−) trans 3-ethoxy carbonyl-4-(4'-fluorophenyl)-N-methyl-piperidine-2,6-dione (I) (1.00 equivalent, 88 mmole) and 69 ml of toluene. This suspension was stirred at room temperature. This solution was transferred to the additional funnel. The imide-ester solution was added dropwise. This resulted in a very exothermic reaction. The feed rate was adjusted to maintain the reaction temperature at below 20° C. After the end of the feed, the 250 ml flask was rinsed with additional toluene, 7 ml, and this was added to the addition funnel. The reaction mixture was heated to 75° C. for three hours, then recooled to 10° C. Additional toluene, 50 ml, was added. The speed of the agitator was increased to 500 RPMs. This was followed by slow addition of 9 ml of water. The reaction mixture got very thick at the end of this addition. Aqueous sodium hydroxide, 15%, 9 ml, was then added dropwise. The solid started to break up at the end of this addition. Water, 18 ml, was then added dropwise. At the end of this feed, the reaction mixture was warmed to 65° C. for twenty minutes and the stirrer was slowed to 350 RPMs. The reaction mixture was then cooled to 40° C., then the byproduct solids were collected on a Büchner funnel. The solids were reslurried with toluene (2×31 ml). The desired product (II) was isolated from the combined filtrates, washed, air dried, then dried in a vacuum desiccator overnight.

This afforded a white solid, yield=16.85 grams, 85.9%.

EXAMPLE 5

Reduction with Sodium Aluminum Hydride/ Lithium Chloride 0.38 Molar

A 500 ml, four-necked, round bottom flask was equipped with a mechanical stirrer, a 125 ml pressure-equalizing addition funnel, a Teflon® stopper and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. Lithium chloride, 9.90 grams (3.24 equivalents, 233.86 mmole) was added. The flask was then charged with tetrahydrofuran, 69 ml. This solution was stirred at 350 RPMs. Sodium aluminum hydride, 11.70 grams of 95% assay (2.70 equivalents, 194.89 mmole) slurried in toluene, 19 ml, was added to the reactor. Additional tetrahydrofuran, 37 ml, was added and this suspension was stirred at room temperature for thirty minutes. This suspension was cooled to 5° C. and stirred for an additional five minutes. A dry, 250 ml, single-necked flask was fitted with a large, egg-shaped magnetic stir bar, and an argon inlet. This flask was purged with argon, then charged with 21.2 grams of (+/−) trans 3-ethoxy carbonyl-4-(4'-fluorophenyl)-N-methyl-piperidine-2,6-dione (I) (1.00 equivalent, 72.2 mmole) and 59 ml of toluene. This suspension was stirred at room temperature. This solution was transferred to the addition funnel. The imide-ester solution was added dropwise. This resulted in a very exothermic reaction. The feed rate was adjusted to maintain the reaction temperature at below 20° C. After the end of the feed, the 250 ml flask was rinsed with additional toluene, 6 ml, and this was added to the additional funnel. The reaction mixture was heated to 75° C. for three hours, then recooled to 10° C.

Additional toluene, 40 ml, was added. The speed of the agitator was increased to 500 RPMs. This was followed by slow addition of 8 ml of water. The reaction mixture got very thick at the end of this addition. Aqueous sodium hydroxide, 15%, 8 ml, was then added dropwise. The solid started to break up at the end of this addition. Water, 16 ml, was then added dropwise. At the end of this feed, the reaction mixture was warmed to 65° C. for thirty minutes and the stirrer was slowed to 350 RPMs. The reaction mixture was then cooled to 30° C., then the byproduct solids were collected on a Büchner funnel. The solids were reslurried with toluene (2×27 ml). The desired product (II) was isolated from the combined filtrates, washed, air dried, then dried in a vacuum desiccator overnight.

This afforded a white solid, yield=13.40 grams, 83.1%.

COMPARATIVE EXAMPLE

Reduction with Sodium Aluminum Hydride/
Lithium Chloride 0.40 Molar

A 500 ml, four-necked, round bottom flask was equipped with a mechanical stirrer, a 125 ml pressure-equalizing addition funnel, a Teflon® stopper and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. Lithium chloride, 10.55 grams (3.15 equivalents, 240.0 mmole) was added. The flask was then charged with tetrahydrofuran, 60 ml. This solution was stirred at 350 RPMS. Sodium aluminum hydride, 13.53 grams of 90% assay (2.86 equivalents, 226.0 mmole) was added, and this suspension was stirred at room temperature for thirty minutes. Toluene, 75 ml, was then added to the reactor. This suspension was cooled to 10° C. and stirred for an additional thirty minutes. A dry, 250 ml, single-necked flask was fitted with a large, egg-shaped magnetic stir bar, and an argon inlet. This flask was purged with argon, then charged with 23.3 grams of (+/−) trans 3-ethoxy carbonyl-4-(4'-fluorophenyl)-N-methyl-piperidine-2,6-dione (I) (1.00 equivalent, 79 mmole) and 50 ml of toluene and 15 ml tetrahydrofuran. This suspension was stirred at room temperature. This solution was transferred to the addition funnel. The imide-ester solution was added dropwise. This resulted in a very exothermic reaction. The feed rate was adjusted to maintain the reaction temperature at below 20° C. The reaction mixture was heated to 65° C. for three hours, then recooled to 10° C. Additional toluene, 47.5 ml, was added. This was followed by slow addition of 9 ml of water. The reaction mixture got very thick at the end of this addition. Aqueous sodium hydroxide, 15%, 9 ml, was then added dropwise. The solid started to break up at the end of this addition. Water, 18.1 ml, was then added dropwise. At the end of this feed, the reaction mixture was warmed to 50° C. for thirty minutes, the reaction mixture was cooled to room temperature, and then the byproduct solids were collected on a Büchner funnel. The solids were reslurried with toluene (2×30 ml). The desired product (II) was isolated from the combined filtrates, washed, air dried, then dried in a vacuum desiccator overnight.

This afforded a white solid, yield=12.70 grams, 72.0%.

The foregoing examples are illustrative of the present invention and are not to be construed as limiting thereof. The invention is defined by the following claims, with equivalents of the claims to be included therein.

That which is claimed is:

1. A process for reducing a compound, comprising:
    reducing a compound, singly or a mixture thereof, of the formula

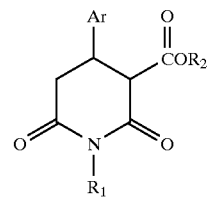

wherein:
    Ar represents an aryl or substituted aryl group

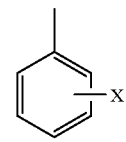

in which X is hydrogen, C1–C4 alkyl, C1–C4 alkoxy, trifluoroalkyl, hydroxy, halogen, methylthio or arylalkyloxy;
    $R^1$ is hydrogen, C1–C4 alkyl, or arylalkyl; and
    $R^2$ is C1–C4 alkyl,
by combining said compound, singly or a mixture thereof, with a reducing agent in a solvent system comprising an ethereal to hydrocarbon solvent ratio of about 40% to about 70% to form a compound, singly or a mixture thereof, of the formula

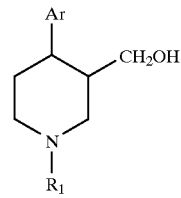

in which $R^1$ and Ar are the same as defined above.

2. The process of claim 1, wherein said reducing agent is selected from the group consisting of lithium aluminum hydride and sodium aluminum hydride with at least one additive.

3. The process of claim 2, wherein said reducing agent is lithium aluminum hydride.

4. The process of claim 2, wherein said reducing agent is sodium aluminum hydride with at least one additive.

5. The process of claim 4, wherein said at least one additive is lithium chloride.

6. The process of claim 1, wherein X is hydrogen or halogen; $R^1$ is hydrogen or C1–C4 alkyl; and $R^2$ is C1–C4 alkyl.

7. The process of claim 6, wherein X is fluorine; $R^1$ is methyl; and $R^2$ is methyl or ethyl.

8. A process for preparing trans-4-(4'-fluorophenyl)-3-hydroxymethyl-N-methylpiperidine, comprising reducing a substrate selected from the group consisting of (+/−) trans 3-ethoxycarbonyl-4-(4'-fluorophenyl)-N-methyl-piperidine-2,6-dione, (+/−) trans 3-methoxycarbonyl-4-(4'-fluorophenyl)-N-methyl-piperidine-2,6-dione, (−) trans 3-ethoxycarbonyl-4-(4'-fluorophenyl)-N-methyl-piperidine- 2,6-dione, (−) trans 3-methoxycarbonyl-4-(4'-fluorophenyl)-N-methyl-piperidine-2,6-dione, and mixtures thereof, by combining said substrate, singly or a mixture thereof, with a reducing agent in a solvent system comprising an ethereal to hydrocarbon solvent ratio of about 40% to about 70%.

9. The process of claim 8, wherein said reducing agent is selected from the group consisting of lithium aluminum hydride and sodium aluminum hydride with at least one additive.

10. The process of claim 9, wherein said reducing agent is lithium aluminum hydride.

11. The process of claim 9, wherein said reducing agent is sodium aluminum hydride with at least one additive.

12. The process of claim 11, wherein said at least one additive is lithium chloride.

13. The process of claim 8, wherein the substrate is (+/−) trans 3-ethoxycarbonyl-4-(4'-fluorophenyl)-N-methyl-piperidine-2,6-dione.

14. The process of claim 8, wherein the substrate comprises (+/−) trans 3-methoxycarbonyl-4-(4'-fluorophenyl)-N-methyl-piperidine-2,6-dione.

15. The process of claim 8, wherein the substrate comprises (−) trans 3-ethoxycarbonyl-4-(4'-fluorophenyl)-N-methyl-piperidine-2,6-dione.

16. The process of claim 8, wherein the substrate comprises (−) trans 3-methoxycarbonyl-4-(4'-fluorophenyl)-N-methyl-piperidine-2,6-dione.

* * * * *

UNITED STATES PATENT AND TRADEMARK OFFICE
CERTIFICATE OF CORRECTION

PATENT NO. : 5,936,090

DATED : August 10, 1999

INVENTOR(S) : Pautard-Cooper et al.

It is certified that error appears in the above-identified patent and that said Letters Patent is hereby corrected as shown below:

Column 2, in the first formula, "$R_2$" should read --$R^2$--; "$R_1$" should read --$R^1$--; in the third formula, "$R_1$" should read --$R^1$--.

Column 8, in the first formula, "$R_2$" should read --$R^2$--; "$R_1$" should read --$R^1$--; in the third formula, "$R_1$" should read --$R^1$--.

Signed and Sealed this

Twentieth Day of June, 2000

Q. TODD DICKINSON

*Attest:*

*Attesting Officer*    *Director of Patents and Trademarks*